(12) United States Patent
Kogel-Hollacher et al.

(10) Patent No.: US 8,410,392 B2
(45) Date of Patent: Apr. 2, 2013

(54) MACHINING DEVICE AND METHOD FOR MACHINING MATERIAL

(75) Inventors: Markus Kogel-Hollacher, Haibach (DE); Christoph Dietz, Obertshausen (DE)

(73) Assignee: Precitec Optronik GmbH, Rodgau (DE)

( * ) Notice: Subject to any disclaimer, the term of this patent is extended or adjusted under 35 U.S.C. 154(b) by 542 days.

(21) Appl. No.: 12/594,765

(22) PCT Filed: Mar. 4, 2008

(86) PCT No.: PCT/EP2008/001692
§ 371 (c)(1),
(2), (4) Date: Feb. 12, 2010

(87) PCT Pub. No.: WO2008/122330
PCT Pub. Date: Oct. 16, 2008

(65) Prior Publication Data
US 2010/0155375 A1     Jun. 24, 2010

(30) Foreign Application Priority Data

Apr. 5, 2007   (DE) .......................... 10 2007 016 444
Jan. 31, 2008  (EP) ...................................... 08001774

(51) Int. Cl.
B23K 15/00   (2006.01)
B23K 26/02   (2006.01)

(52) U.S. Cl. ......... 219/121.18; 219/121.19; 219/121.29; 219/121.62; 219/121.83

(58) Field of Classification Search ............ 219/121.61–121.72, 121.8, 121.81, 219/121.83, 121.13–121.29; 324/307, 316
See application file for complete search history.

(56) References Cited

U.S. PATENT DOCUMENTS

| 5,920,373 | A  | * | 7/1999 | Bille .............................. 351/212 |
| 6,053,613 | A  |   | 4/2000 | Wei et al. |
| 7,595,895 | B2 | * | 9/2009 | Kurita et al. ................... 356/614 |
| 2006/0084957 | A1 | * | 4/2006 | Delfyett et al. ................. 606/12 |
| 2006/0179992 | A1 | * | 8/2006 | Kermani ......................... 83/651 |
| 2008/0058780 | A1 |   | 3/2008 | Vogler |

FOREIGN PATENT DOCUMENTS

| DE | 101 55 203 | 6/2003 |
| EP | 0 956 809  | 11/1999 |
| EP | 1 231 496  | 8/2002 |
| EP | 1 886 758  | 2/2008 |

OTHER PUBLICATIONS

International Search Report issued in corresponding International application PCT/EP2008/001692 dated Jul. 11, 2008.
Furlong et al., "Scanning Lenses and Systems", CVI Melles Griot, 4 pages, date unknown, prior art admitted.

* cited by examiner

*Primary Examiner* — Samuel M Heinrich
(74) *Attorney, Agent, or Firm* — Lempia Summerfield Katz LLC

(57) ABSTRACT

The invention relates to a machining device (10) comprising at least one machining head (16) designed to provide at least one high-energy machining beam (22), especially an electron or laser beam. Such a machining device is used to remove material from workpieces (28) or for connecting workpieces (28) by bonding, especially by means of welding. According to the invention, at least one scanning device (32) designed as an optical coherence tomograph and provided for surface scanning is associated with the machining head (16). The invention also relates to a method for machining material using a high-energy machining beam for scanning surface areas of a workpiece which is machined, not yet machined, or being machined, by means of an optical coherence tomograph.

6 Claims, 4 Drawing Sheets

MACHINING DEVICE AND METHOD FOR MACHINING MATERIAL

RELATED APPLICATION DATA

This U.S. national phase application is based on international application no. PCT/EP2008/001692 filed on Mar. 4 2008, which claimed priority to German patent application 10 2007 0016 444.2 filed on Apr. 5, 2007 and European patent application 08001774.2 filed on Jan. 31, 2008. Priority benefit of these earlier filed applications is hereby claimed, and the full disclosures of these earlier filed applications are hereby incorporated by reference herein.

BACKGROUND

1. Field of the Disclosure

The invention relates to a machining device with at least one machining head which is designed to provide at least one high-energy machining beam, in particular an electron beam or a laser beam.

2. Description of the Related Art

A machining device known from the market makes a relative motion possible between one or more workpieces to be machined and the machining head, in order to enable an eroding and/or joining machining of material. The machining head is equipped with an integrated or separately constructed source of the high-energy machining beam, for example a laser beam or an electron beam. Typical fields of application for a machining device of such a type are the eroding of material of a workpiece by means of a laser beam, or the welding of plastic parts or metal parts by means of an electron beam or a laser beam. Depending on the field of application, stringent quality demands are made of machining processes of such a type, which also require, inter alia, an exact guidance of the high-energy machining beam in relation to the workpiece, as well as a monitoring of the result of machining on the workpiece. For this purpose, a known machining device can be provided with one or more sensor devices which, using optical measuring methods (for example, light-slit methods) and/or electrical measuring methods (for example, eddy-current methods) and/or acoustic measuring methods (for example, ultrasonic methods), enable an examination of the result of machining that is necessary for quality control.

Since the sensors for the application of the known measuring methods are greatly influenced by the high-energy machining beam and/or require a mechanical contact with the surface being machined, a minimal spacing has to be maintained between the machining location of the machining beam and the measuring point at which the respective measuring method is applied. Consequently a process control for the machining beam can only take place with a time delay. The time delay results from the speed of machining and the geometrical spacing between machining location and measuring location.

SUMMARY

The object of the invention consists in making available a measuring device and a method that enable an improved process control for the process of machining with the high-energy machining beam.

With respect to the measuring device, this object is achieved, in accordance with the invention, by a machining device with the features of claim 1.

Advantageous configurations of the invention are the subject-matter of dependent claims.

In accordance with the invention, the machining device is configured in such a manner that at least one scanning device taking the form of an optical coherence tomograph which is provided for a surface scanning is assigned to the machining head.

By the term 'optical coherence tomograph' a measuring device is understood which, with the aid of an interferometer, utilises the coherence properties of light —that is to say, the capacity of light for interference. For this purpose there is provision to separate beams of light emitted from a broadband light-source into two ray bundles with the aid of a beam-splitter device, in particular with a semitransmitting mirror. The first ray bundle is guided in a reference arm which has a known, adjustable length. The ray bundle is reflected at the end within the reference arm, is guided again within the reference arm and subsequently coupled into a detector. The second ray bundle is conducted to the surface to be gauged and is reflected there again at least partly in the direction of the coherence tomograph. The reflected light is likewise coupled into the detector in the coherence tomograph and results therein in interference with the first ray bundle. From the measuring signal generated by the detector, information can be acquired as to how long the path from the beam-splitter to the detector was for the second ray bundle. From this, a spacing between the coherence tomograph and the surface to be gauged can be ascertained.

Instead of a beam-splitter—in plate form or in cube form, for example—a fibre coupler with two separate fibre bundles which serve for coupling out the two ray bundles may also be employed.

Depending on the technical design of the coherence tomograph, a measurement takes place sequentially (in time-encoded manner) or simultaneously (spatially encoded) in the time domain or in the frequency domain. For a design of a coherence tomograph for measuring in the frequency domain in the case of time-encoded measurement, a light-source with variable wavelength, in particular a tunable laser, is employed instead of a broadband light-source provided for the other designs.

In accordance with the invention, the optical coherence tomograph is utilised for contactless scanning of a surface geometry of an opaque surface. Information about structures that are located beneath the opaque surface, on the other hand, is not acquired with the method according to the invention.

The surface scanning is effected one-, two- or three-dimensionally. A one-dimensional surface scanning provides a spacing from the coherence tomograph to the scanned surface. A two-dimensional surface scanning provides a surface contour, i.e. a line-like surface profile of the scanned surface. A three-dimensional surface scanning provides a planar image—that is to say, a surface relief of the scanned surface.

The scanning of the surface is effected with the aid of a measuring beam of light which is emitted by the coherence tomograph and reflected on the surface to be gauged. The reflected light is at least partly reflected back into the optical coherence tomograph and conducted to a detector together with a reference beam of light. Therein, surface-geometry information is acquired on the basis of the interference between the reflected portions of the measuring beam of light and the reference beam of light.

Optical coherence tomography exhibits a high resolution for the spatial geometry of the surface that is to be examined. In addition, a spacing between the machining location defined by the high-energy machining beam and the measuring location at which the surface scanning by the optical coherence tomograph takes place can be chosen to be very small, preferentially infinitesimally small. Hence only a small, in particular infinitesimal, temporal offset also obtains between machining and ascertainment of the surface, so an advantageous process control can be implemented.

Experiments have shown that the surface scanning with the aid of optical coherence tomography is not perturbed, or at worst is perturbed insignificantly, by the very bright process light which generally arises in the course of machining with high-energy process light. This is a significant advantage in comparison with other measuring methods, in which the process light in optical detectors or similar swamps out the actual measuring signals.

In one configuration of the invention there is provision that an optical reference path provided for the scanning device is guided in an optical fibre. In the case of a known reference path, which is guided as a free beam between several optical elements, stringent demands made of the quality and alignment of the optical elements that are used for this purpose have to be satisfied. In the case of guidance of the optical reference path in an optical fibre, in particular in a plastic or glass fibre, an inexpensive and compact style of construction for the reference path is achieved.

In a further configuration there is provision that the optical fibre of the reference path is applied, in particular wound, onto an expanding body which is capable of being driven by a control device. For the purpose of implementing the optical coherence tomography, a time-dependent change in the length of the reference path is necessary, which can be realised by elastic expansion of the optical fibre. For this purpose, the optical fibre of the reference path is applied onto an expanding body. The expanding body is preferentially produced from a piezoelectric material and changes its volume as a result of application of a control voltage, by which the applied optical fibre is influenced in its length. Preferentially the expanding body is of cylindrical construction and wrapped with one or more layers of the optical fibre, so that a particularly homogeneous expansion of the fibre is guaranteed.

In a further configuration of the invention, a length of the optical reference path is chosen in such a manner that a spacing between an exit plane of a measuring beam and a surface to be gauged may amount to more than 100 mm, preferentially more than 250 mm, particularly preferably more than 500 mm, in particular more than 800 mm. Consequently a contactless detection of the geometry of the surface to be machined that is being machined at the moment, or of the surface that has already been machined, is possible with a spacing that is adapted to a working spacing between a front end of the machining head facing towards the workpiece and the workpiece. Hence by virtue of the scanning device no restriction arises with regard to the positioning of the machining head in relation to the workpiece. In this connection, the expression 'exit plane of the measuring beam of the optical coherence tomograph' designates that plane in which the measuring beam emitted from the optical coherence tomograph in the direction of the workpiece becomes a free beam—that is to say, is no longer passing through any optical element.

In a preferred embodiment of the invention, the optical reference path is changed in its length in such a manner that a measuring range of the optical coherence tomograph along its optical axis directed towards the workpiece amounts to at least 3 mm, preferentially at least 5 mm, particularly preferably at least 8 mm. For this purpose the reference path is expanded by a similar amount of length, in particular by an identical amount of length. This means that, in the case of an expansion of the reference path by 8 mm, depth information of the scanned surface can be acquired within an interval of 8 mm.

In a further configuration of the invention, a deflecting device is provided on the scanning device, which is designed for a deflection of the measuring beam out of the scanning device onto the object of measurement and for a deflection of reflected beams emanating from the object of measurement into the scanning device. With a deflecting device the measuring beam can be guided over the surface of the workpiece independently of a relative motion between the machining head and the workpiece. Hence, for example, a spacing between a point of incidence of the high-energy machining beam on the workpiece and a measuring point of the measuring beam on the surface of the workpiece can be varied. In order to enable a detection of the surface geometry of the workpiece, there is provision furthermore to couple the beams reflected from the object of measurement at least partly into the scanning device with the deflecting device, so that the optical paths for the measuring beam and for the reflected beams are alike.

In a further configuration of the invention, the deflecting device exhibits at least one movably suspended mirror which is capable of being driven by a control device. The mirror is provided for a deflection of the measuring beam and of the reflected beams and can be swivelled in one or more directions in space in order to bring about a one-dimensional or two-dimensional relative motion of the measuring beam in relation to the surface of the workpiece, in order to enable a linear or planar scanning of the surface of the workpiece. In a preferred embodiment of the invention, the mirror is suspended on gimbals and is swivelled in several directions in space by several piezoelectric actuating elements that are capable of being driven independently of one another.

In a further configuration of the invention, an f-theta objective is arranged in the beam path between the mirror and the object of measurement. In the case of an f-theta objective, the image height is proportional to an input angle that an incident parallel bundle of light includes with the optical axis. In accordance with the invention, there is assigned to the f-theta objective a mirror on which the measuring beam impinges in such a manner that the swivelling of the measuring beam caused by the mirror causes a linear motion of the focal point of the measuring beam in a plane. By this means, the precise scanning of substantially flat surfaces is made possible, since, in contrast to a swivelling of the measuring beam relative to the surface to be scanned, no angle dependence of the reflected beams reflected from the surface arises. Rather, the measuring beam always impinges on the surface to be gauged with the same orientation and can, in the same way, also be reflected back into the coherence tomograph by the f-theta objective and the mirror and conducted to the detector together with the reference beam of light.

In a further configuration of the invention, a light-source, in particular a superluminescent diode with a wavelength of more than 900 nm, preferentially more than 1200 nm, particularly preferably 1350 nm, is provided by way of illuminating means for the scanning device. A superluminescent diode ordinarily has a coherence length from 10 nm to 50 nm and provides beams of light with a bandwidth of approximately 10 nm to 25 nm around a principal wavelength.

In a further configuration of the invention, the scanning device is integrated into the machining head in such a manner that at least one optical component is capable of being used jointly by the machining beam and by the measuring beam. In the case of the optical component that is used jointly, it is preferentially a question of a lens or a protecting glass. The lens may, in particular, have been provided for the focusing of the machining beam and of the measuring beam of light, in order to enable an adaptation to differing spacings between workpiece and machining head. The protecting glass serves to protect the optical system of the machining head and of the optical coherence tomograph. To the protecting glass there may be assigned devices provided on the machining head, such as outlets for protective gas or temperature sensors, which are intended to prevent a contamination and/or an overheating of the protecting glass. As a result, influences that arise by virtue of the machining of material can be effectively kept away from the scanning device. In this connection it may a question, for example, of vapours and/or particles of material that emanate from the weld and that, without appropriate protective mechanisms, would result in an impairment of the measuring quality of the scanning device.

In a further configuration of the invention, an at least substantially matching arrangement of a machining plane of the machining beam and a scanning plane of the measuring beam is provided. In the course of a surface machining by the machining beam, the latter is focused in such a manner that a focal point at least substantially coincides with the point of incidence of the machining beam on the surface to be machined. In accordance with the invention, the scanning device is likewise focused in such a way that the focal point of the measuring beam of light coincides with the focal point of the machining beam. Preferentially the machining beam and the measuring beam of light exhibit a confocal arrangement, i.e. their focal points coincide. In a particularly preferred version of the invention, the machining beam emerging from the machining head and the scanning beam emitted from the scanning device are arranged coaxially, so that a gauging of the machining point defined by the machining beam is made possible by the scanning device.

With respect to the method, the object formulated in the introduction is achieved by a method as disclosed and described herein. In accordance with the invention, an unmachined region of material is scanned with a measuring beam of an optical coherence tomograph, and an evaluation of the surface topography is undertaken on the basis of at least one reflected beam reflected from the workpiece. A scanning of such a type may, for example, be provided in order to be able to determine exactly the contour of a weld gap to be joined by welding and consequently to compensate tolerances in the contour of the weld gap that can be balanced out by the machine control of the machining device. In this connection, a compensation both with regard to a power density and with regard to a positioning of the focal point of the machining beam can be undertaken.

In particular, when an erosion of material in the axial direction of the machining beam is detected in the course of the scanning by the optical coherence tomograph, either the focal point can be tracked in the axial direction or the workpiece can be readjusted along the axial direction. Such an erosion of material arises, for example, regularly in the course of laser drilling. Since the high-energy machining beam is, as a rule, focused precisely to a predeterminable machining point, without an appropriate tracking due to the change of position of the working location a reduction of the efficiency of the erosion of material arises. The tracking of the focal point can in this case be brought about, for example, by changing a focal length of an optical system generating the focal point and arranged in a machining head, and/or by relocation of the machining head.

In supplement, or alternatively, with the method according to the invention there is provision to scan the working region of the high-energy machining beam and to implement a process control on the basis of the information acquired by the scanning. This is of significance both in the case of material-eroding methods, in particular laser cutting, and in the case of material-joining methods, in particular laser welding, and in the case of generating methods, in particular laser deposition welding, by means of the machining beam. In the case of an erosion of material, by virtue of the scanning of the working region it can be established immediately whether the desired surface structure has been obtained by the erosion of material. In the case of a joining of material, in particular by electron-beam welding or laser-beam welding, the surface geometry of the weld seam that is generated can be scanned, in order to obtain, by adaptation of welding parameters such as power density and pulse duration for the machining beam, a reliable joining of the materials with slight thermal influence.

In supplement, or alternatively, with the aid of the scanning device an already machined region of material can be scanned, in order to be able—for example, after cooling of the weld seam—to assess a warpage of material caused by the thermal influences and, where appropriate, to implement an adaptation of welding parameters.

BRIEF DESCRIPTION OF THE DRAWINGS

An exemplary embodiment of the invention will be described in more detail below on the basis of the drawing. Shown therein are.

DETAILED DESCRIPTION OF THE DISCLOSURE

Figure 1:
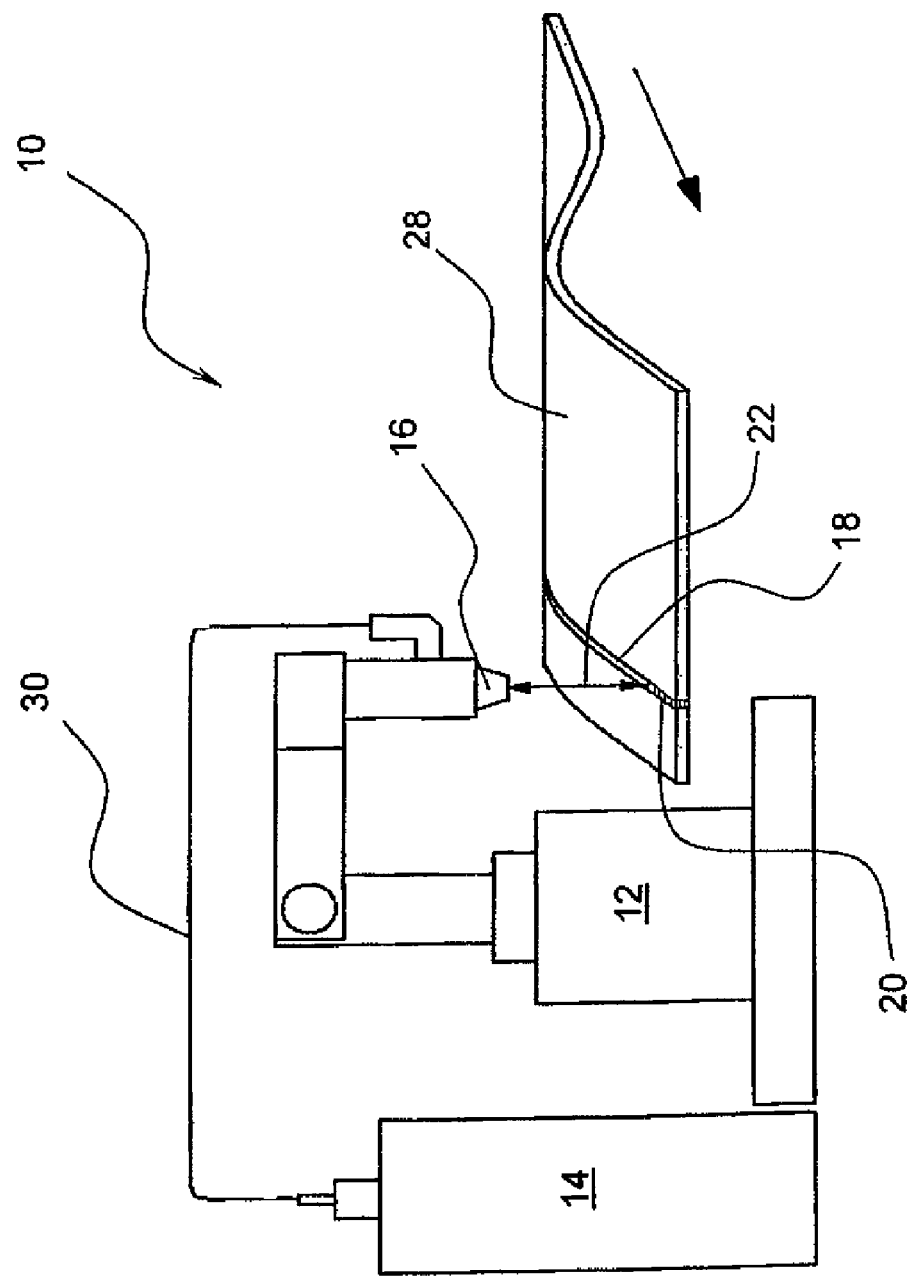
FIG. 1: a schematic representation of a machining device for laser welding with an industrial robot.

In FIG. 1 a machining device 10 is represented which is substantially composed of an industrial robot 12 and a laser-source 14 as well as a machining head 16 borne by the industrial robot 12. The industrial robot 12 is a multi-axis robot which can bring the machining head 16 into various spatial positions relative to the workpiece 28 in order to guarantee an advantageous machining of the workpiece 28. The laser-source 14 is connected to the machining head 16 by means of a flexible glass-fibre line 30. In this case the laser light generated by the laser-source 14 is coupled into an optical system which is provided in the machining head 16 and which is not represented in any detail in FIG. 2. Emanating from the optical system, the laser light is directed onto the workpiece 28 in the form of a high-energy machining beam 22.

Figure 2:
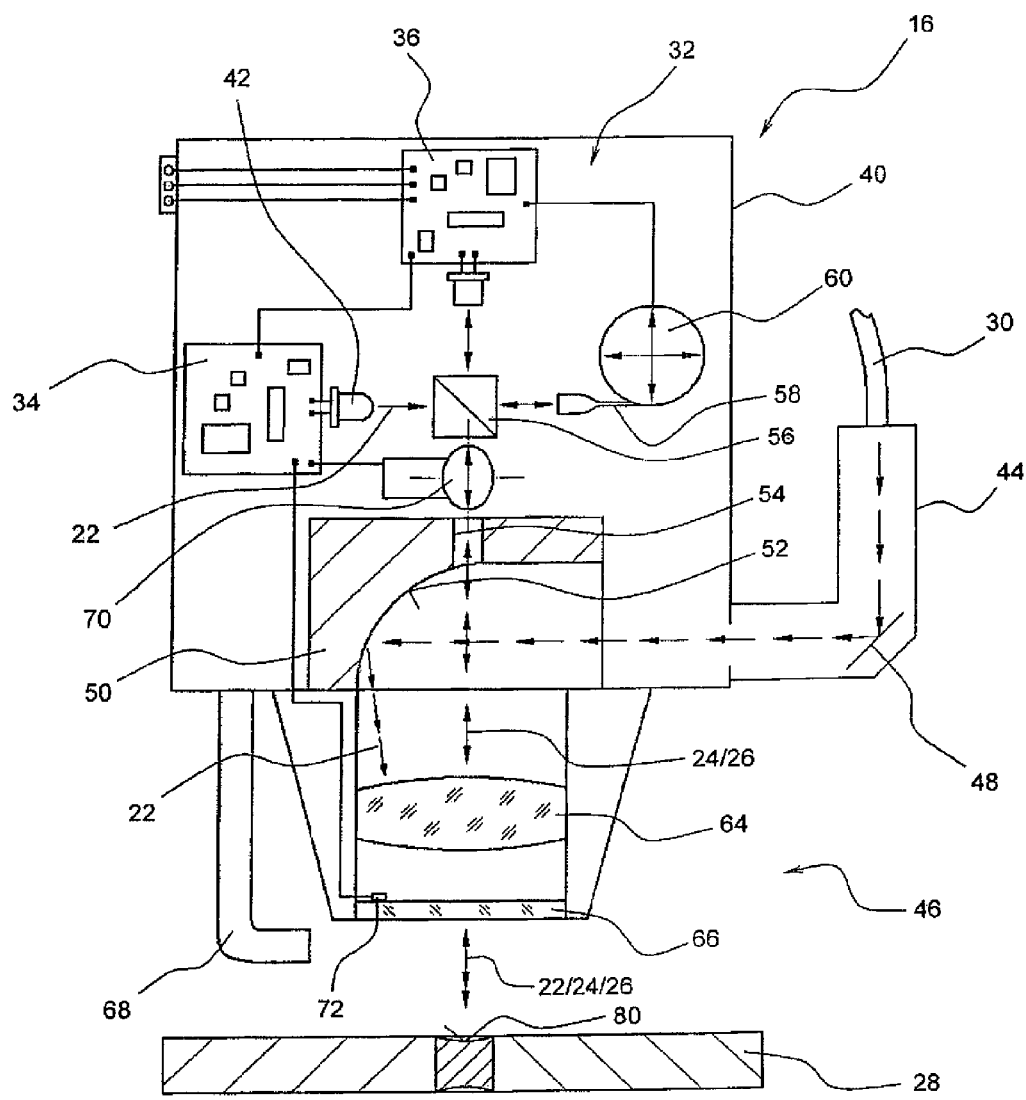
FIG. 2: a schematic representation of the optical coherence tomograph integrated within the machining head.

Arranged in the machining head 16 in addition to the optical system for the high-energy machining beam 22 is an optical coherence tomograph 32, which is not represented in any detail in FIG. 2 and which is provided for an ascertainment of a surface structure generated by the welding operation in the region of the weld gap 18 and/or the weld seam 20. For the planned machining operation the workpiece 28 is displaced in a machining direction indicated in FIG. 1 while the machining head 16 is maintained at a substantially constant spacing and in a substantially vertical position in relation to the workpiece 28 with the aid of the industrial robot 12.

The machining head 16 represented schematically in FIG. 2 in the manner of a block diagram comprises two systems operating substantially independently of one another. A first optical system serves for conveying the high-energy machining beam 22 provided by the laser-source 14. For this purpose, a redirecting device 44 is provided on the housing 40, which exhibits a redirecting mirror 48 for right-angled redirection of the laser beam coupled out of the glass-fibre line 30. Moreover, a focusing block 50 is provided for focusing the laser beam onto the machining location 80 on the workpiece 28. For this purpose the focusing block 50 exhibits a mirror surface 52 which is concavely curved in sections and which focuses the incident expanded laser beam so that the latter forms a focal spot on the workpiece 28.

In addition, the focusing block 50 is provided with a through-bore 54 which enables a passage of a measuring beam 24 of the optical coherence tomograph 32 which, in accordance with FIG. 2, is arranged above the focusing block 50. Moreover, the through-bore 54 also permits a passage of reflected light which is reflected back on the surface of the workpiece 28 in the direction of the optical coherence tomograph 32.

The optical coherence tomograph 32 includes a superluminescent diode 42 which is electrically connected to a control circuit 34 and radiates light with a wavelength of approximately 1300 nm in the direction of a beam-splitter 56. At the beam-splitter 56, which is constructed as a semitransmitting mirror, the light emitted from the superluminescent diode 42 is partly transmitted in the direction of a reference arm 58. A further part of the light emitted by the superluminescent diode 42 is reflected on the beam-splitter 56 in the direction of the workpiece 28 and forms a measuring arm.

The reference arm 58 is formed by a glass-fibre winding which is applied on a spool core 60 manufactured from piezoelectric material. The spool core 60 is, in turn, electrically connected to an evaluating circuit 36, in order by applying an electrical voltage to bring about a purposeful expansion of the spool core 60 and consequently an expansion of the glass-fibre winding of the reference arm 58. The change of length of the reference arm 58, which can be carried out in exemplary manner with a frequency of 200 Hz and with an expansion of 8 mm for the reference arm 58, changes the propagation-time of the light of the superluminescent diode 42 coupled into the reference arm 58.

By interaction of the light coupled into the reference arm 58 with the reflected beam 26 reflected back from the workpiece 28, an interference of the two beams of light, i.e. an addition or a subtraction of the light-waves, takes place. The light intensity arising in this connection can be ascertained by a photodiode 62 which is connected to the evaluating circuit 36. With knowledge of the length of the reference arm 58 obtaining instantaneously in the given case, and of the light intensity obtaining at the photodiode 62, an inference can be drawn as to the spacing between the optical coherence tomograph 32 and the surface of the workpiece 28, so that, given suitable guidance of the measuring beam 24, a surface profile of the workpiece 28 can be ascertained.

Although during the welding operation by action of the high-energy machining beam 22 on the workpiece 28 both a backscattering of the laser light reflected on the workpiece 28 and an emission of secondary light caused by thermal radiation take place, an immediate determination of the surface profile in the region of the weld or of the machining location can be realised through the use of the optical coherence tomograph 32. The primary light of the machining beam 22 backscattered from the workpiece 28 and the secondary light emitted from the heated workpiece 28 do not satisfy the coherence condition of the measuring light emitted with a short coherence length from 10 nm to 50 nm, such as is required for an interference with the light of the superluminescent diode 42 coupled into the reference arm 58.

As represented schematically in FIG. 2, the high-energy machining beam 22, the measuring beam 24 and the reflected beam 26 reflected back into the optical coherence tomograph 32 are arranged coaxially relative to one another. For an adjustment of the size of the focal spot that the high-energy machining beam exhibits on the surface of the workpiece 28, a focusing lens 64, which is displaceable in the vertical direction in accordance with FIG. 2 and which is driven by an actuating device which is not represented, is mounted in the optical system for the high-energy machining beam 22.

The measuring beam 24 can be redirected with the aid of a deflecting device 70 which takes the form of a swivelling mirror with two swivel axes oriented orthogonally relative to one another, in order to enable a planar scanning of the surface of the workpiece 28.

In order to protect the entire optical system, both of the high-energy machining beam 22 and of the optical coherence tomograph 32, against undesirable environmental influences such as may arise in particular by virtue of vapours and particles emanating from the weld, a covering glass 66, which is produced from a thermally stable, optically transparent material, is mounted on a lower end face of the machining head 16. The covering glass 66 may, where appropriate, be provided with a filter coating that is transmitting merely for the light wavelengths of the machining beam 22, of the measuring beam 24 emitted from the superluminescent diode 42 and of the reflected beam 26. Assigned to the covering glass 66 is a temperature sensor 72 which is electrically connected to the control circuit 34 and which serves for detection of a thermal overload of the covering glass 66. Moreover, mounted on the machining head 16 is a jet pipe 68 which is able to conduct a current of protective gas, oriented transversely relative to the optical axis of the reflected beam 26 and of the measuring beam 24, over the covering glass 66, in order to prevent a precipitation of vapours or melt particles emanating from the weld pool.

Figure 3:
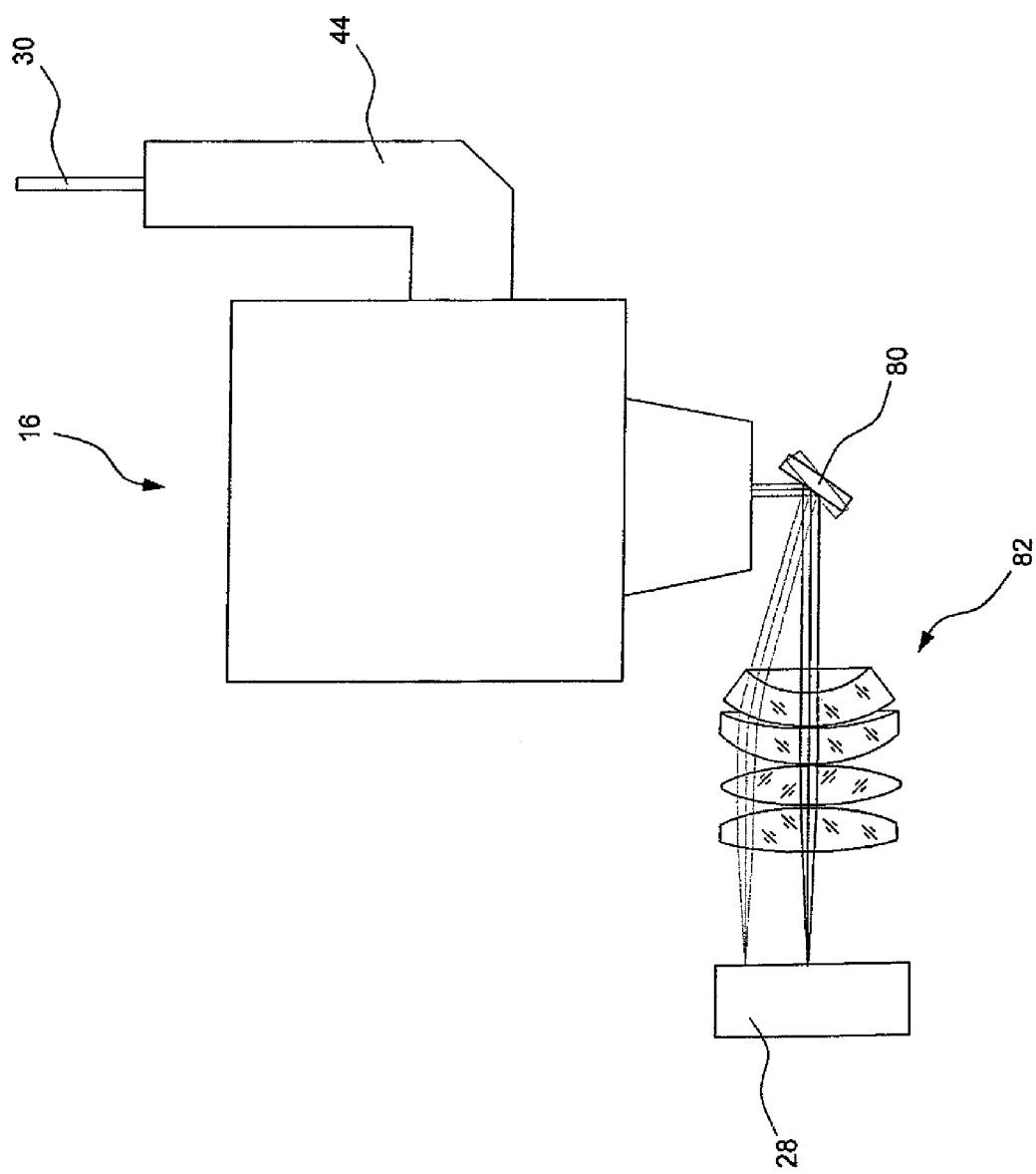
FIG. 3: a schematic representation of a combination of a swivelling mirror with an f-theta objective arranged in the beam path of the machining head.

Assigned to the machining head 16 represented in more detail in FIG. 3, which has the same structure as the machining head 16 represented in FIG. 2, is a plane swivelling mirror 80 and also an f-theta lens arrangement 82 arranged in the beam path between swivelling mirror 80 and object of measurement 28. In contrast to the machining head 16 represented in FIG. 2, the optical system of the machining head 16 according to FIG. 3 is set up for the output of a parallel beam. The swivelling mirror 80 can be swivelled by means of actuators, which are not represented, about an axis of rotation which is arranged in a mirror plane facing towards the measuring beam on the surface of the swivelling mirror 80 and which, according to the representation of FIG. 3, extends orthogonally relative to the plane of the drawing. For the purpose of clarifying the mode of action of the f-theta lens arrangement 82, the measuring beam emerging from the machining head 16 is represented as a parallel beam but may, depending on the refractive power of the f-theta lens, also be provided in the form of a diverging or converging beam.

The measuring beam impinges on the swivelling mirror 80 and is deflected appropriately by the latter. The measuring beam impinging on the f-theta lens arrangement 82 at differing angles and at differing locations is converted by the refractive action of the f-theta lens arrangement 82 into a focused measuring beam, the principal ray of which always extends parallel to the optical axis of the f-theta lens arrangement 82. In the exemplary embodiment represented in FIG. 3, the surface of the object of measurement 28 to be scanned lies in the focal plane of the measuring beam. Hence in the course of a swivelling of the swivelling mirror 80 about the swivel axis a linear surface region of the object of measurement 28 can always be scanned with constant focusing of the measuring beam. If the swivelling mirror 80 is additionally capable of swivelling about a further swivel axis situated in the plane of the drawing and arranged orthogonally to that described above, then on account of the lenses of the f-theta lens arrangement 82, which are constructed in rotationally symmetrical manner, a two-dimensional surface scanning of the object of measurement 28 can be undertaken.

Figure 4:
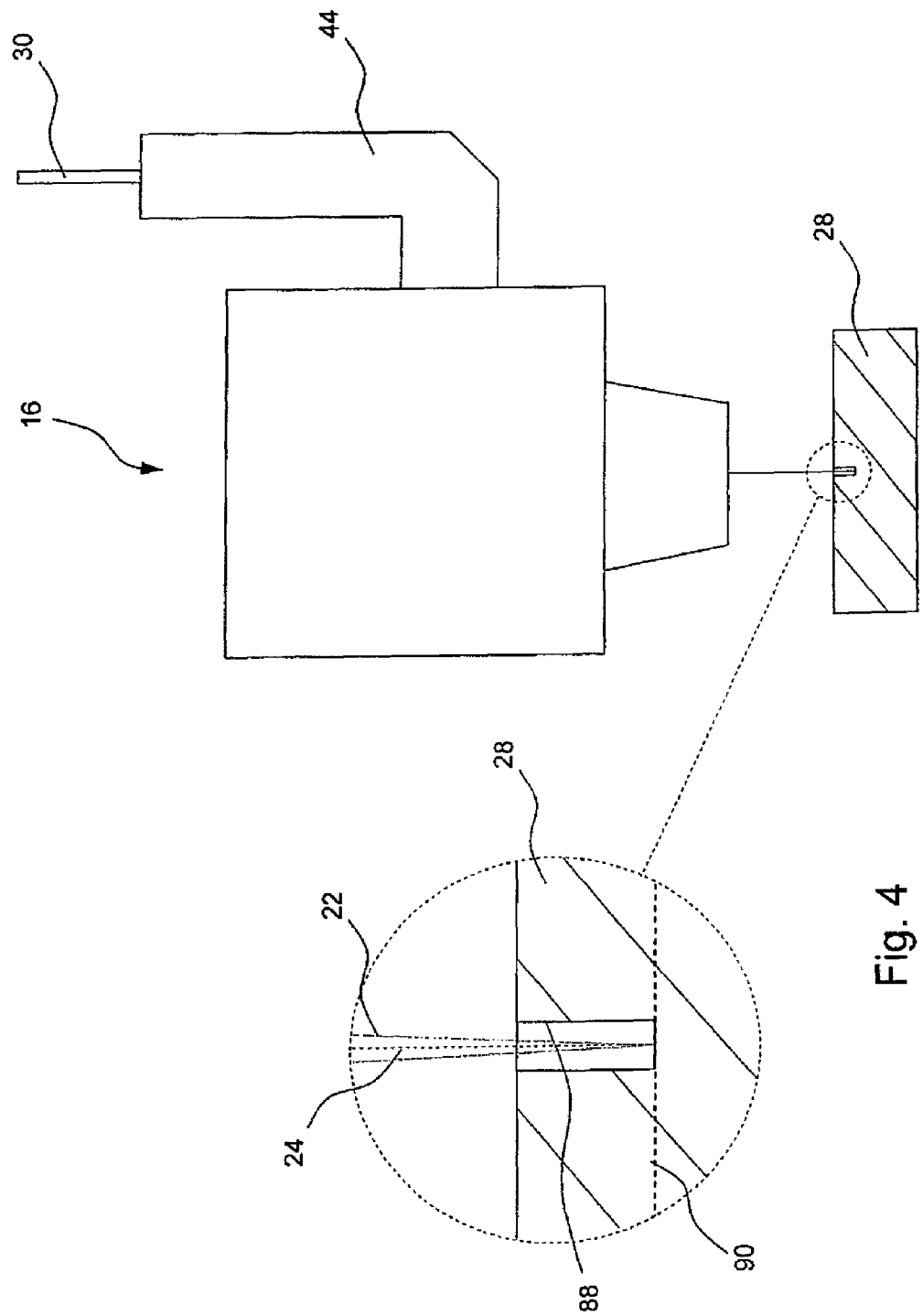
FIG. 4: a schematic representation of a use of the machining head for a drilling operation.

In the case of the use, represented schematically in FIG. 4, of the machining head 16 for a drilling operation, in the enlarged detail view the machining beam 22 and also the measuring beam 24 which enter a bore 88 are represented. The machining beam 22 is focused to a focal point 90. In the representation according to FIG. 4 the focal point 90 is situated at the level of the bottom of the borehole and accordingly coincides with the position of the working location at which the erosion of material by means of the machining beam 22 takes place. Consequently the machining beam 22 impinges on the working location with maximum energy density and can erode the material with maximum efficiency.

Since the working location is relocated by the erosion of material, without a regulation of the focal position for the machining beam 22 a reduction of the energy density occurs, since the machining beam 22 impinges on the working location in defocused manner. In order to avoid this, on the basis of the measuring beam 24 and the distance information to be ascertained therefrom there is provision to regulate the spacing between machining head 16 and working location in such a way that the focal point 90 is always situated at the level of the working location. For the purpose of changing the spacing, the machining head 16 and/or the workpiece can be relocated. Additionally or alternatively, the focal point can be changed by an optical system (focusing lens [64] 62 in FIG. 2) which generates the focal point and is arranged in the machining head.

The invention claimed is:

1. A machining device comprising:
   at least one machining head which is configured to produce a high-energy machining beam,
   an optical coherence tomograph which is configured to produce a measuring beam and to measure a distance between the machining head and a workpiece to be machined by the machining device,
   a scanning device which
     is configured to direct the measuring beam on various locations on the workpiece,
     comprises a movably suspended mirror which is capable of being driven by a control device and
     comprises an f-theta objective which is arranged in a beam path between the mirror and the workpiece.

2. The machining device of claim 1, wherein the scanning device is integrated into the machining head in such a manner that at least one optical component is capable of being used jointly by the machining beam and by the measuring beam.

3. The machining device of claim 1, wherein a focal plane of the machining beam and a scanning plane of the measuring beam at least substantially coincide.

4. The machining device of claim 1, wherein the optical coherence tomography comprises an optical reference path having a length which is chosen such that a spacing between the machining head and the workpiece is greater than 100 mm.

5. The machining device of claim 4, wherein the spacing is greater than 500 mm.

6. The machining device of claim 5, wherein the spacing is greater than 800 mm.

\* \* \* \* \*